United States Patent [19]

Pirolo et al.

[11] Patent Number: 6,063,335
[45] Date of Patent: May 16, 2000

[54] METHOD FOR DISINFECTING SURFACES

[75] Inventors: Robert S. Pirolo, Tacoma, Wash.; J. Frederick Hessel, Doylestown, Pa.

[73] Assignee: Henkel Corporation, Gulph Mills, Pa.

[21] Appl. No.: 09/027,384

[22] Filed: Feb. 20, 1998

Related U.S. Application Data

[60] Provisional application No. 60/041,661, Mar. 24, 1997.

[51] Int. Cl.[7] .................................................. A61L 2/00
[52] U.S. Cl. ............................ 422/28; 424/128; 514/724; 426/332; 426/335
[58] Field of Search .............................. 422/28; 426/332, 426/335; 424/128; 514/724

[56] References Cited

U.S. PATENT DOCUMENTS

| | | | |
|---|---|---|---|
| 4,500,559 | 2/1985 | Bender et al. | 426/646 |
| 4,556,571 | 12/1985 | Swartz et al. | 426/265 |
| 4,592,892 | 6/1986 | Ueno et al. | 422/28 |
| 5,032,310 | 7/1991 | McIntosh, Sr. | 252/106 |
| 5,069,922 | 12/1991 | Brotsky et al. | 426/332 |
| 5,143,739 | 9/1992 | Bender et al. | 426/332 |
| 5,192,570 | 3/1993 | Bender et al. | 426/332 |
| 5,262,186 | 11/1993 | Bender et al. | 426/332 |
| 5,266,690 | 11/1993 | McCurry, Jr. et al. | 536/18.6 |
| 5,268,185 | 12/1993 | Bender et al. | 426/92 |
| 5,283,073 | 2/1994 | Bender et al. | 426/332 |
| 5,354,568 | 10/1994 | Bender et al. | 426/332 |
| 5,449,763 | 9/1995 | Wulff et al. | 536/18.6 |
| 5,512,309 | 4/1996 | Bender et al. | 426/332 |
| 5,635,231 | 6/1997 | Bender et al. | 426/332 |
| 5,700,507 | 12/1997 | Bender et al. | 426/332 |

FOREIGN PATENT DOCUMENTS

| | | |
|---|---|---|
| 1779262 | 11/1992 | U.S.S.R. . |
| 1834903 | 8/1993 | U.S.S.R. . |

OTHER PUBLICATIONS

Ladd, T.I. and Costerton, J.W., "Methods for Studying Biofilm Bacteria", Methods in Microbiology, Academic Press Limited, 1990, vol. 22, pp. 285–307.

MacDonald, K. L., et al., JAMA, 1988, 259:3567–3570.

Abrishami, et al., "Bacterial Adherence And Viability On Cutting Board Surfaces", Journal of Food Safety, 1994, 14:153–172.

*Primary Examiner*—Krisanne Thornton
*Attorney, Agent, or Firm*—John E. Drach; Henry E. Millson, Jr.

[57] ABSTRACT

A surface is disinfected with a solution containing a fully or partially neutralized orthophosphate and optionally one or more surfactants. The method provides a safe and effective means of sanitizing surfaces such as cutting boards by removing, reducing or retarding the growth of pathogenic microorganisms without the use of substances that are toxic to humans.

14 Claims, No Drawings

METHOD FOR DISINFECTING SURFACES

CROSS-REFERENCE TO RELATED APPLICATION

This application claims the benefit of earlier filed and copending provisional application Ser. No. 60/041,661, filed on Mar. 24, 1997, the entire contents of which are incorporated herein by reference.

STATEMENT REGARDING FEDERALLY SPONSORED RESEARCH OR DEVELOPMENT

Not Applicable.

BACKGROUND OF THE INVENTION

Infections acquired from contaminated food and food products are becoming more and more frequent. For example, a 1987 study of group health patients with diarrhea in the Puget Sound area showed an unexpectedly high incidence of E. coli 0157:H7 (MacDonald K L, et al, JAMA 259:3567–3570, 1987). Eighty-nine percent of the patients with E. coli did not have a history of eating undercooked meat. In 1993 there was an E. coli 0157:H7 epidemic traced to undercooked hamburger meat in Washington state. Four children died and several others suffered permanent kidney damage. Much of this contamination has been traced to the food preparation process, although two of the Washington E. coli cases did not come from direct consumption of contaminated hamburgers and are assumed to have been acquired by indirect contact. Other bacteria causing gastroenteritis and diarrhea include Campylobacter, Salmonella and Shigella species. Salmonella typhimurium has been reported in watermelon, dried milk, and baby formula and led to severe cases of diarrhea. Salmonella enteritides is showing a marked increase in incidence due to contamination of eggs and egg products. With the apparent proliferation of illnesses caused by ingestion of pathogenic organisms, there is a greater potential for cross contamination of foods such as from cutting boards and other work surfaces that are used for processing and/or preparing poultry, beef, or pork.

A number of recent studies have shown that bacterial contamination of cutting boards that come into direct or indirect contact with food is due principally to bacterial biofilms and not planktonic bacteria. Planktonic bacteria are single organisms moving in a fluid while a bacterial biofilm consists of colonies of bacteria surrounded by a mucous, glycopolysaccharide coat which is adherent to surfaces. Most of the studies of classical microbiology starting with Louis Pasteur have been performed on bacteria growing in enriched liquid culture media or on solidified enriched culture media in petri dishes. These enriched culture conditions encourage bacteria to grow in planktonic form. In nature, bacteria exist in a more hostile environment and form biofilms. One example of a biofilm is Legionella bacteria in air conditioner cooling towers which is responsible for Legionaries disease. Bacteria on wood cutting boards rapidly form biofilms which are not recovered by routine culture methods and are difficult to remove from contaminated areas.

While it is generally accepted that cutting boards can be cleaned using conventional methods such as hot water and detergents and/or disinfectants such as quaternary ammonium compounds, a study published in January 1994 showed that there were living bacteria in biofilms adherent to wood and plastic cutting boards and suggested these bacteria were a potential source for household and commercial food contamination. This article concluded that there is a need for development of better ways to remove bacterial biofilms from cutting surfaces (Abrishami, Tall et al "Bacterial Adherence and Viability on Cutting Board Surfaces," J Food Safety 14:153–172, 1994.)

SUMMARY OF THE INVENTION

One aspect of the present invention pertains to a method for treating a surface such as cutting boards and the like that come into direct or indirect contact with food to remove, reduce or retard the growth of pathogenic microorganisms such as E. coli, salmonella, campylobacter, shigella and listeria. The method according to the invention comprises contacting a surface with an effective amount of a contacting solution comprised of a fully or partially neutralized orthophosphate or a combination thereof. Another aspect of the present invention pertains to a method for treating a surface such as cutting boards and the like that come into direct or indirect contact with food to remove, reduce or retard the growth of pathogenic microorganisms such as E. coli, salmonella, campylobacter, shigella and listeria. The method according to the invention comprises contacting a surface with an effective amount of a contacting solution comprised of a fully or partially neutralized orthophosphate or a combination thereof and one or more surfactants. The present invention provides a safe and effective method of sanitizing surfaces such as cutting boards by removing, reducing or retarding the growth of pathogenic microorganisms without the use of substances that are toxic to humans.

DESCRIPTION OF THE PREFERRED EMBODIMENTS

The term disinfect as used herein means to remove, reduce or retard the growth of pathogenic microorganisms such as pathogenic bacteria and yeast.

Trialkali metal phosphate is an orthophosphate salt of the formula $M_3PO_4$ wherein M is an alkali metal or hydrogen as described in U.S. Pat. No. 5,354,568, the entire contents of which are incorporated herein by reference. The orthophosphate useful in the method according to the invention is any one or a mixture of a partially or completely neutralized phosphate salts such as mono-hydrogen disodium phosphate, di-hydrogen mono-sodium phosphate and trisodium phosphate and the hydrates thereof such as the dodecahydrate as described in U.S. Pat. No. 5,354,568. The most preferred orthophosphate salts are $Na_3PO_4$ and trisodium phosphate dodecahydrate ($Na_3PO_4 \cdot 12H_2O$).

The amount of orthophosphate in the contacting solution is an effective amount which can be any amount that is effective to remove, reduce or retard the growth of pathogenic microorganisms on a surface. The amount of orthophosphate in the contacting solution can be any amount necessary to render the treatment solution effective to remove, reduce or retard the growth of pathogenic microorganisms on a surface and will typically vary from about 1% by weight to the solubility limit or saturation point of the orthophosphate in the solution. The pH of the treatment solutions can vary from about 7 to about 14 with the preferred range being from about 9 to about 11.

Another embodiment of the method according to the invention comprises the use of a contacting solution comprised of a surfactant and an orthophosphate as described above. The surfactant can be any nonionic, anionic, cationic, or amphoteric surfactant or a combination of such surfactants. Examples of nonionic surfactants that can be used in the compositions and methods according to the invention include but are not limited to alkylene oxide condensates of alkyl phenols, alkylene oxide condensates of aliphatic alcohols, alkylene oxide condensates of aliphatic amines, amine oxides, alkanolamides, and the like. Examples of anionic surfactants which can be used in the compositions and methods according to the invention include but are not limited to such anionic surfactants as carboxylates, sulfonates, sulfates, phosphates, and alkyl benzene sulfonates. Examples of cationic surfactants that can be used in the compositions and methods according to the invention include but are not limited to quaternary ammonium compounds such as quaternized amines and the like. The amphoteric surfactants that can be used in the compositions and methods according to the invention include but are not limited to betaines, imidazolinium compounds, amino acids and the like. A preferred surfactant type is a surfactant that is non-toxic or exhibits low toxicity and is biodegradable. An alkyl polyglycoside is a particularly preferred surfactant because it is non-toxic, is completely biodegradable and is made from regrowable raw materials. The alkyl polyglycosides which can be used in the invention have the formula I $$R_1O(R_2O)_b(Z)_a \qquad \text{I}$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6. Preferred alkyl polyglycosides which can be used in the compositions and processes according to the invention have the formula I wherein Z is a glucose residue and b is zero. Such alkyl polyglycosides are commercially available, for example, as APG®, GLUCOPON®, PLANTAREN® or AGRIMUL® surfactants from Henkel Corporation, Ambler, Pa. 19002. Examples of such surfactants include but are not limited to:

1. GLUCOPON® 220 Surfactant—an alkyl polyglycoside in which the alkyl group contains 8 to 10 carbon atoms and having an average degree of polymerization of 1.5.
2. GLUCOPON® 225 Surfactant—an alkyl polyglycoside in which the alkyl group contains 8 to 10 carbon atoms and having an average degree of polymerization of 1.7.
3. GLUCOPON® 600 Surfactant—an alkyl polyglycoside in which the alkyl group contains 12 to 16 carbon atoms and having an average degree of polymerization of 1.4.
4. GLUCOPON® 625 Surfactant—an alkyl polyglycoside in which the alkyl group contains 12 to 16 carbon atoms and having an average degree of polymerization of 1.4.
5. APG® 325 Surfactant—an alkyl polyglycoside in which the alkyl group contains 9 to 11 carbon atoms and having an average degree of polymerization of 1.6.
6. PLANTAREN® 2000 Surfactant—an alkyl polyglycoside in which the alkyl group contains 8 to 16 carbon atoms and having an average degree of polymerization of 1.4.
7. PLANTAREN® 1300 Surfactant—an alkyl polyglycoside in which the alkyl group contains 12 to 16 carbon atoms and having an average degree of polymerization of 1.6.
8. AGRIMUL® PG 2067 Surfactant—an alkyl polyglycoside in which the alkyl group contains 8 to 10 carbon atoms and having an average degree of polymerization of 1.7.

Other examples include alkyl polyglycoside surfactant compositions which are comprised of mixtures of compounds of formula I as described in U.S. Pat. Nos. 5,266,690 and 5,449,763, the entire contents of both of which are incorporated herein by reference.

The amount of surfactant in the treatment solutions of the present embodiment of the process according to the invention can be any amount necessary to render the treatment solution effective to remove, reduce or retard the growth of pathogenic microorganisms on a surface and will typically vary from about 1% to about 75% by weight of the total treatment solution and preferably from about 7.0% to about 15% by weight.

While the process according to the invention can be used to disinfect any surface, a hard surface such as wood or plastic is preferred. The process according to the invention is especially applicable to disinfecting cutting boards on which foods such as chicken, beef and fish are cut or otherwise manipulated prior to cooking or some other operation such as freezing. In carrying out the process according to the invention, a surface such as wood or plastic is contacted with an aqueous solution comprised of one or more trialkali metal phosphates or a solution comprised of one or more trialkali metal phosphates and one or more surfactants as described herein. The cleaning and disinfecting of a surface can be accomplished by any conventional method used to clean surfaces such as by means of a brush or a cloth wetted with the treating solution or by immersion of the surface in the treating solution or contacting the surface within a conventional automatic dishwasher for a period of time sufficient to remove, retard or reduce bacterial contamination and/or growth over and above that obtainable if pure water were used. A surface is treated with a treatment solution containing from about 4% to saturation, preferably from about 6% and more preferably from about 8% to saturation of trialkali metal orthophosphate by weight of solution. A treatment solution comprised of a surfactant and a trialkali metal orthophosphate, can contain from about 4% to saturation, preferably from about 6% and more preferably from about 8% to saturation of trialkali metal orthophosphate and from about 1% to about 70% of a surfactant. Most preferably, a treatment solution will typically contain from about 5% to about 8% by weight and from about 7.0% to about 15% by weight of an alkyl polyglycoside. The pH of the treatment solutions can vary from about 7 to about 14 with the preferred range being from about 9 to about 11. The treatment solutions according to the invention can also contain other components such as defoamers and disinfectants such as quaternary ammonium compounds.

The following examples are meant to illustrate but not the invention.

EXAMPLE 1

About 50 ul drop dilution MIC of each treatment solution listed below was deposited onto lawn blood plate cultures of the following bacteria:

| | |
|---|---|
| E. coli - E. coli 0157: HE | Pseu a - Pseudomonas aeruginosa |
| Sale typh- Salmonella typhi | Shig - Shigella dysenterica |
| Staph a - Staphylococcus aureus | Strep p- Streptococcus pyogenes |

In addition to the component listed below, each treatment solution contained the following (wt %): 10% PLANTAREN® 2000[1]; 7% PLANTAREN® 1200[2]; 4% TRITON® N 101[3]; 2% VELVETEX® BK-35[4]; 2% cocamide diethanolamide.

1)=5% trisodium phosphate
2)=1% trisodium phosphate

3)=1% dimethyl alkyl benzalkonium chloride
4)=0.5% dimethyl alkyl benzalkonium chloride
5)=1% trisodium phosphate +1% of the mono-n-butyl ether of 1,2-dipropylene glycol
1—PLANTAREN® 2000 Surfactant—a 50% actives alkyl polyglycoside in which the alkyl group contains 8 to 16 carbon atoms and having an average degree of polymerization of 1.4, a trademark product of Henkel Corporation, Gulph Mills, Pa.
2—PLANTAREN® 1200 Surfactant—a 50% actives alkyl polyglycoside in which the alkyl group contains 12 to 16 carbon atoms and having an average degree of polymerization of 1.4, a trademark product of Henkel Corporation, Gulph Mills, Pa.
3—TRITON® N 101, a 100% actives ethoxylated nonylphenol, a trademark product of Union Carbide Corp.
4—VELVETEX® BK-35, a 35% actives cocoamidopropyl betaine, a trademark product of Henkel Corporation, Gulph Mills, Pa.

The results are given in Table 1 below:

TABLE 1

| Organism | 1) | 2) | 3) | 4) | 5) |
|---|---|---|---|---|---|
| Sal typh | $10^0$ | $10^0$ | — | — | $10^0$ |
| E. coli | $10^0$ | — | — | — | — |
| Pseu a | $10^0$ | — | — | — | — |
| Shig | $10^0$ | — | — | — | — |
| Staph a | $10^{-1}$ | $10^0$ | $10^{-1}$ | $10^{-1}$ | $10^0$ |
| Strep p | $10^{-4}$ | $10^{-1}$ | $10^{-2}$ | $10^{-2}$ | $10^{-2}$ |

Zones of inhibition - expressed to greatest dilution
$10^0$–$10^{-8}$ = dilutions tested
— = no zone, no inhibition

EXAMPLE 2

A sufficient number of wood and plastic cutting board samples were each inoculated with a suspension of E. coli 0157:H7 ATCC #35150 in 50% horse serum and 10% vegetable oil. Similarly, additional cutting board samples were inoculated with a suspension of S. typhimurium ATCC #14028 in 50% horse serum and 10% vegetable oil. The cutting board samples were allowed to dry for 1 hour and then were treated with one of the three treatment solutions below, or with sterile PBS (phosphate buffered saline) as a control. At approximately 1 hour or at 18–22 hours following treatment, the recoverable microbial population on each of the cutting board surfaces was determined.

In addition to the component listed below, each treatment solution contained the following (wt %): 10% PLANTAREN® 2000[1]; 7% PLANTAREN® 1200[2]; 4% TRITON® N 101[3]; 2% VELVETEX® BK-35[4]; 2% cocamide diethanolamide.
1)=5% or 7.5% trisodium phosphate (see below)
2)=FORTECH® Cleaner[5]+2500 ppm or 200 ppm hypochlorite bleach (see below)
3)=5000 ppm dimethyl alkyl benzalkonium chloride
4)=0.05M aq. PBS
1—PLANTAREN® 2000 Surfactant—a 50% actives alkyl polyglycoside in which the alkyl group contains 8 to 16 carbon atoms and having an average degree of polymerization of 1.4, a trademark product of Henkel Corporation, Gulph Mills, Pa.
2—PLANTAREN® 1200 Surfactant—a 50% actives alkyl polyglycoside in which the alkyl group contains 12 to 16 carbon atoms and having an average degree of polymerization of 1.4, a trademark product of Henkel Corporation, Gulph Mills, Pa.
3—TRITON® N 101, a 100% actives ethoxylated nonylphenol, a trademark product of Union Carbide Corp.
4—VELVETEX® BK-35, a 35% actives cocoamidopropyl betaine, a trademark product of Henkel Corporation, Gulph Mills, Pa.
5—FORTECH® Cleaner is a trademark product of Formula, Corp., Seattle, Wash.

E. coli and S. typhimurium cultures were used to inoculate separate Tryptic Soy Agar (TEA) plates. Plates were incubated at 30–35° C. for approximately 24 hours to develop confluent growth. The growth from each of the cultures was suspended separately in a solution comprised of 50% horse serum (Northbay Bioscience catalog #550-100; 2×100 mL), 10% vegetable oil (Crisco Oil) and 40% PBS. The suspensions were used the same day of preparation. The population of each of the prepared microbial suspensions were determined immediately prior to inoculating the cutting board samples. Aliquots of each microbial suspension were serially diluted in sterile PBS, and plated in triplicate using the pour plate method and Tryptic Soy Agar. The plates were allowed to solidify, inverted and incubated at 30–35° C. for 48 to 72 hours. Following incubation, the colonies per plate were enumerated, and the average number of colony-forming units (CFU's) per mL of suspension were determined for each of the two inocula. A total of sixteen autoclaved cutting board samples (8 wood and 8 plastic) were inoculated with 1.0 mL each of the E. coli test suspension. Sixteen additional autoclaved cutting board samples (8 wood and 8 plastic; 5×5 cm each) were inoculated with 1.0 mL of the S. typhimurium test suspension. The inoculated cutting board samples were allowed to dry in a bioflow hood for approximately 1 hour. (Time=–1 hour) Two of the wood and two of the plastic cutting board samples inoculated with the E. coli suspension were washed with sterile gauze saturated with a cutting board cleaner for 10 seconds. A similar procedure was carried out for the cutting board samples inoculated with the S. typhimurium suspension. The Fortech cleaner was followed by a 10 second wash with a sterile gauze sponge saturated in dilute bleach. Each of the samples were rinsed with sterile water. (Time=0 hours) The washed surfaces were allowed to dry for approximately 1 hour. The microbial population of one of the wood and one of the plastic cutting board samples previously inoculated with E. coli was determined approximately one hour after washing (Time=1 hour). Each cutting board sample was placed in a separate sterile specimen cup containing a minimum of 50 mL of sterile PBS. The surfaces were scraped with a sterile scalpel, and the surface and scrapings sonicated in a bath sonicator for approximately 1 minute. The sterile PBS container with the cutting board sample was mixed by vortex mixing for about 60 seconds. Serial dilutions were prepared for each test surface in sterile PBS and plated in triplicate using the pour plate method and TEA. The plates was incubated at 30–35° C. for 48–72 hours. Steps 1 and 2 were repeated for the remaining samples inoculated with E. coli at approximately 18–22 hours after washing, (Time=19 hours). The samples were allowed to remain in the bioflow hood during the interim period. The procedure in sections 2 and 3 were repeated for the washed cutting board samples previously inoculated with the S. typhimurium suspension. Following incubation the pour plates were examined for bacterial growth and the average number of Colony-Forming Units (CFU's) recovered from each cutting board sample was determined and recorded.

A second experiment was performed using wood cutting board samples inoculated with E. coli, treatment solution (1)

with 7.5% TSP and treatment solution (2) with 200 ppm hypochlorite were used.

The following schematic describes the testing performed:

| Cleaner | Cutting Board type | Wash 10 sec, $H_2O$ rinse | Microbial assay 1 hr | 18 hr |
|---|---|---|---|---|
| *Escherichia coli* ATCC #35150 | | | | |
| | | Inoculate with *E. coli* wait 1 hr | | |
| Control | wood | + | + | + |
| PBS | wood | + | + | + |
| | plastic | + | + | + |
| | plastic | + | + | + |
| (1) with | wood | + | + | + |
| 5% TSP | wood | + | + | + |
| | plastic | + | + | + |
| | plastic | + | + | + |
| (2) with | wood | + | + | + |
| 200 ppm | wood | + | + | + |
| bleach | plastic | + | + | + |
| | plastic | + | + | + |
| (3) | wood | + | + | + |
| | wood | + | + | + |
| | plastic | + | + | + |
| | plastic | + | + | + |
| *Salmonella typhimurium* ATCC #14028 | | | | |
| | | Inoculate with S. tphi wait 1 hr | | |
| Control | wood | + | + | + |
| PBS | wood | + | + | + |
| | plastic | + | + | + |
| | plastic | + | + | + |
| (1) with | wood | + | + | + |
| 5% TSP | wood | + | + | + |
| | plastic | + | + | + |
| | plastic | + | + | + |
| (2) with | wood | + | + | + |
| 200 ppm | wood | + | + | + |
| bleach | plastic | + | + | + |
| | plastic | + | + | + |
| (3) | wood | + | + | + |
| | wood | + | + | + |
| | plastic | + | + | + |
| | plastic | + | + | + |
| *E. coli* ATCC #35150 Second experiment: | | | | |
| | | Inoculate with *E. coli* wait 1 hr | | |
| Control | wood | + | + | + |
| (1) as above | wood | + | + | + |
| (2) as above | wood | + | + | + |
| (3) | wood | + | + | + |

The table below summarizes the results of the experiments with a 10 second wash with the three cutting board cleaning formulas described above followed by a sterile water rinse on 5×5 cm wood and on 5×5 cm plastic cutting board samples inoculated with *Escherichia coli* 0157:H7 ATCC #350150 and *Salmonella typhimurium* ATCC #14028.

| | | % Reduction Wood | % Reduction Plastic |
|---|---|---|---|
| *E. coli* Inoc | | | |
| $8.12 \times 10^8$ | (1) with 5% TSP | 95.2 | 99.97 |
| | (3) | 95.4 | 99.91 |
| | (2) with 2500 bl[1]. | 85.0 | 99.97 |
| $2.54 \times 10^9$ | (1) with 7.5% TSP | 93.0 | ND |
| | (3) | 56.0 | ND |
| | (2) with 200 bl. | 24.0 | ND |
| *S. typhimurium* Inoc | | | |
| $2.54 \times 10^9$ | (1) with 5% TSP | 94.3 | 99.97 |
| | (3) | 94.6 | 99.96 |
| | (2) with 2500 bl. | 23.6 | 99.99 |

[1]ppm bleach

What is claimed is:

1. A method for treating the surface of a wooden cutting board which comprises contacting said surface with a disinfecting effective amount of a contacting solution comprised of a disinfectant consisting of a fully or partially neutralized orthophosphate or a combination thereof, wherein said orthophosphate has the formula $M_3PO_4$ in which each M is hydrogen or an alkali metal, provided at least one M is alkali metal, and, optionally at least one quaternary ammonium compound.

2. The method of claim 1 wherein the fully neutralized orthophosphate is trisodium phosphate.

3. The method of claim 1 wherein the amount of fully or partially neutralized orthophosphate is from about 1% by weight to about the solubility limit of said orthophosphate in said solution.

4. A method for treating a surface which comprises contacting a surface with a disinfecting effective amount of a contacting solution comprised of a disinfectant consisting of a fully or partially neutralized orthophosphate or a combination thereof and one or more surfactants, wherein said orthophosphate has the formula $M_3PO_4$ in which each M is hydrogen or an alkali metal, provided at least one M is alkali metal, and, optionally at least one quaternary ammonium compound.

5. The method of claim 4 wherein said surfactant is a nonionic surfactant.

6. A method for treating the surface which comprises contacting a surface with a disinfecting effective amount of a contacting solution comprised of a disinfectant consisting of a trisodium orthophosphate and an alkyl polyglycoside of the formula I $$R_1O(R_2O)_b(Z)_a \quad \quad \text{I}$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6, and, optionally at least one quaternary ammonium compound.

7. A method for treating a surface which comprises contacting a surface with a disinfecting effective amount of a contacting solution comprised of a disinfectant consisting of from about 4% to about 8% by weight of trisodium orthophosphate and from about 7.0% to about 15% by weight of an alkyl polyglycoside of the formula I $$R_1O(R_2O)_b(Z)_a \qquad I$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6, and, optionally at least one quaternary ammonium compound.

8. A method for disinfecting a hard surface comprising contacting said surface with an aqueous solution comprised of a fully or partially neutralized orthophosphate or a combination thereof, wherein the orthophosphate is the only disinfecting component thereof, and wherein the orthophosphate has the formula $M_3PO_4$ in which each M is hydrogen or an alkali metal, provided at least one M is alkali metal.

9. The method of claim 8 wherein the amount of fully or partially neutralized orthophosphate is from about 1% by weight to about the solubility limit of said orthophosphate in said solution.

10. The method of claim 4 wherein one or more surfactants is also present in the aqueous solution.

11. The method of claim 10 wherein said surfactant is an alkyl polyglycoside of the formula I $$R_1O(R_2O)_b(Z)_a \qquad I$$

wherein $R_1$ is a monovalent organic radical having from about 6 to about 30 carbon atoms; $R_2$ is a divalent alkylene radical having from 2 to 4 carbon atoms; Z is a saccharide residue having 5 or 6 carbon atoms; b is a number having a value from 0 to about 12; a is a number having a value from 1 to about 6.

12. The method of claim 4 wherein the orthophosphate is the only disinfecting component in said solution.

13. The method of claim 6 wherein the orthophosphate is the only disinfecting component in said solution.

14. The method of claim 7 wherein the orthophosphate is the only disinfecting component in said solution.

* * * * *